United States Patent [19]

Boyce et al.

[11] 4,169,712

[45] Oct. 2, 1979

[54] SOLAR ENERGY COLLECTION AND UTILIZATION SYSTEM

[76] Inventors: James R. Boyce, Rte. 3, Box 201, Orlando, Fla. 32811; Erich A. Farber, 1218 NE. 5th St., Gainesville, Fla. 32601

[21] Appl. No.: 805,446

[22] Filed: Jun. 10, 1977

[51] Int. Cl.² .............................. C10J 3/00; C02C 1/14
[52] U.S. Cl. .................................. 48/197 A; 48/111; 48/209; 210/180; 126/415; 126/424
[58] Field of Search ............... 48/111, 61, 209, 197 A; 126/270, 271; 210/2, 180, 119; 203/DIG. 1; 60/641

[56] References Cited

U.S. PATENT DOCUMENTS

| | | | |
|---|---|---|---|
| 2,236,350 | 3/1941 | Hoyt | 210/119 |
| 2,760,920 | 8/1956 | Olsen | 126/271 |
| 2,902,028 | 9/1959 | Manly | 126/271 |
| 3,052,229 | 9/1962 | Wenger | 126/271 |
| 3,501,381 | 3/1970 | Delano | 203/DIG. 1 |
| 3,620,206 | 11/1971 | Harris, Jr. et al. | 126/271 |
| 3,924,604 | 12/1975 | Anderson | 126/270 |
| 3,933,628 | 1/1976 | Varani | 126/271 |
| 3,993,458 | 11/1976 | Antal, Jr. | 48/209 |
| 4,020,827 | 5/1977 | Broberg | 126/271 |
| 4,050,907 | 9/1977 | Brimhall | 48/111 |
| 4,055,499 | 10/1977 | Laxo | 210/119 |
| 4,057,401 | 11/1977 | Boblitz | 48/111 |

Primary Examiner—S. Leon Bashore
Assistant Examiner—George C. Yeung
Attorney, Agent, or Firm—Duckworth, Hobby, Allen & Pettis

[57] ABSTRACT

A solar energy collection and utilization system includes a reservoir having a heat transfer fluid stored therein, and a platform supported by the fluid. A solar energy collector is carried by the platform, the system further including a fluid conductor in the collector for receiving energy collected from solar radiation and heating the heat transfer fluid passing therethrough. Appropriate piping is provided between the reservoir and the fluid conductor such that the fluid heated by the collector is stored in the reservoir for subsequent use for heating applications, including methane generation in a separate facility.

24 Claims, 7 Drawing Figures

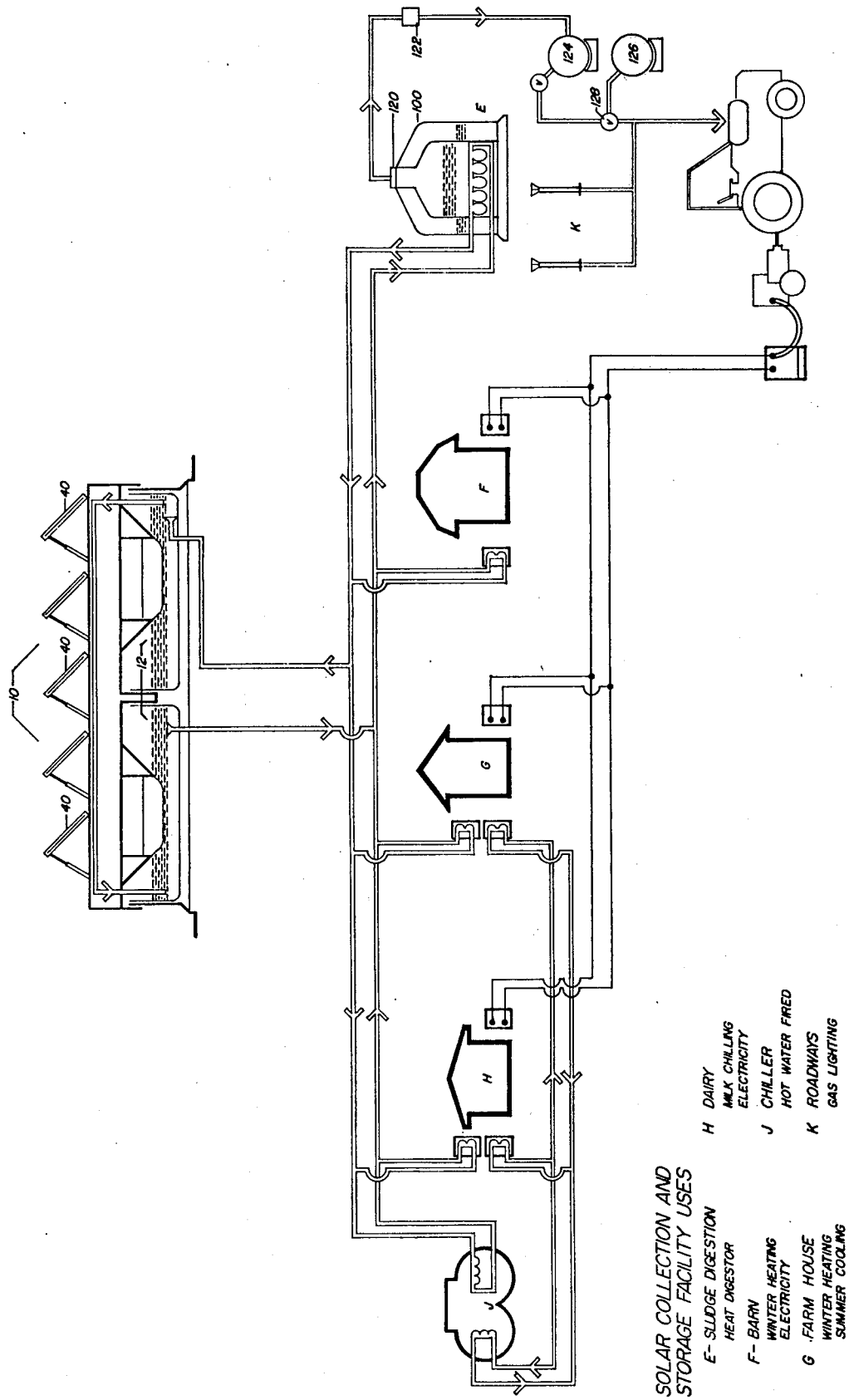

SOLAR ENERGY COLLECTION AND UTILIZATION SYSTEM

BACKGROUND OF THE INVENTION

1. Field of the Invention

The present invention relates to solar energy collection systems, and in particular relates to such systems which are useful in converting heat into other energy forms.

2. Description of the Prior Art

Solar energy collectors as taught in the prior art fall into two general categories. First, so called flat plate collectors generally comprise a relatively planar heat absorbing medium, through which a heat transfer fluid is passed to absorb the incident heat radiation. Examples of flat plate collectors are disclosed in the following U.S. Pat. Nos. 2,907,318 to Awot; 3,780,262 to Rudd; 3,961,619 to Estes, et al; 2,202,756 to Cline; 1,801,710 to Abbot; and 4,007,728 to Guba. These patents are merely representative of a large number of flat plate collector designs which have many uses, primarily for the heating of water for domestic hot water storage facilities.

Other flat plate collectors of interest are useful for heating water in swimming pools and other containers, as is disclosed in the following U.S. Pat. Nos. 3,893,443 to Smith; 3,949,095 to Pelehack; 3,945,059 to Allocco; and 3,279,527 to Hardy.

Customarily, flat plate collectors of the type described above are maintained in a relatively stationary position and rely on the planar nature of the collector to heat the transfer fluid throughout the solar day.

A second category of solar collectors are those which are generally characterized as concentrators. These arrangements generally take the form of parabolic dishes or troughs, in which the heat transfer fluid is pumped through a conduit passing through a focal point of the concentrator. Such arrangements must be pointed in the direction of the sun in order to achieve efficient utilization. Examples of such arrangements are disclosed in the following U.S. Pat. Nos. 3,847,136 to Salvail; 3,321,012 to Hervey; 3,923,039 to Falbel; 1,424,932 to Moreau; and 1,575,309 to Anderson. These patents are likewise merely representative of prior art solar energy concentrators.

In U.S. Pat. No. 3,924,604, Anderson discloses the use of a solar concentrator employing reflectors bouyantly supported upon a fluid for the purpose of producing a Fresnel approximation of a large area reflector.

SUMMARY OF THE INVENTION

The present invention contemplates a solar energy collector and utilization system comprising, in combination, a reservoir having a heat transfer fluid stored therein. A platform is provided and is supported by the fluid, with a solar energy collector carried by the platform. Fluid conducting means in the solar collector is provided for receiving energy collected from solar radiation and heating a fluid passing therethrough. Means are provided to communicate between the reservoir and the fluid conducting means whereby the fluid is heated by the collector and then stored in the reservoir. In a preferred embodiment, the solar energy collector comprises a plurality of conventional flat plate collectors, the system being provided with means for tracking the sun by pointing the flat plate collectors in a general direction toward the sun, and thereby increasing the overall efficiency of the solar collection system. This pointing means includes the provision for rotation of the fluid-supported platform, and means for elevating one edge of each of the collectors.

Further in accordance with the preferred embodiment of the present invention, a slurry tank having a heat exchanger therein which is coupled to the reservoir so as to pass the heated fluid through the heat exchanger to heat to between 90° and 95° F. an organic waste slurry contained within the tank over a period of time and effect digestion of the slurry and generation of methane gas. The generated methane gas is then collected and stored for subsequent uses.

THE DRAWING

Figure 2:
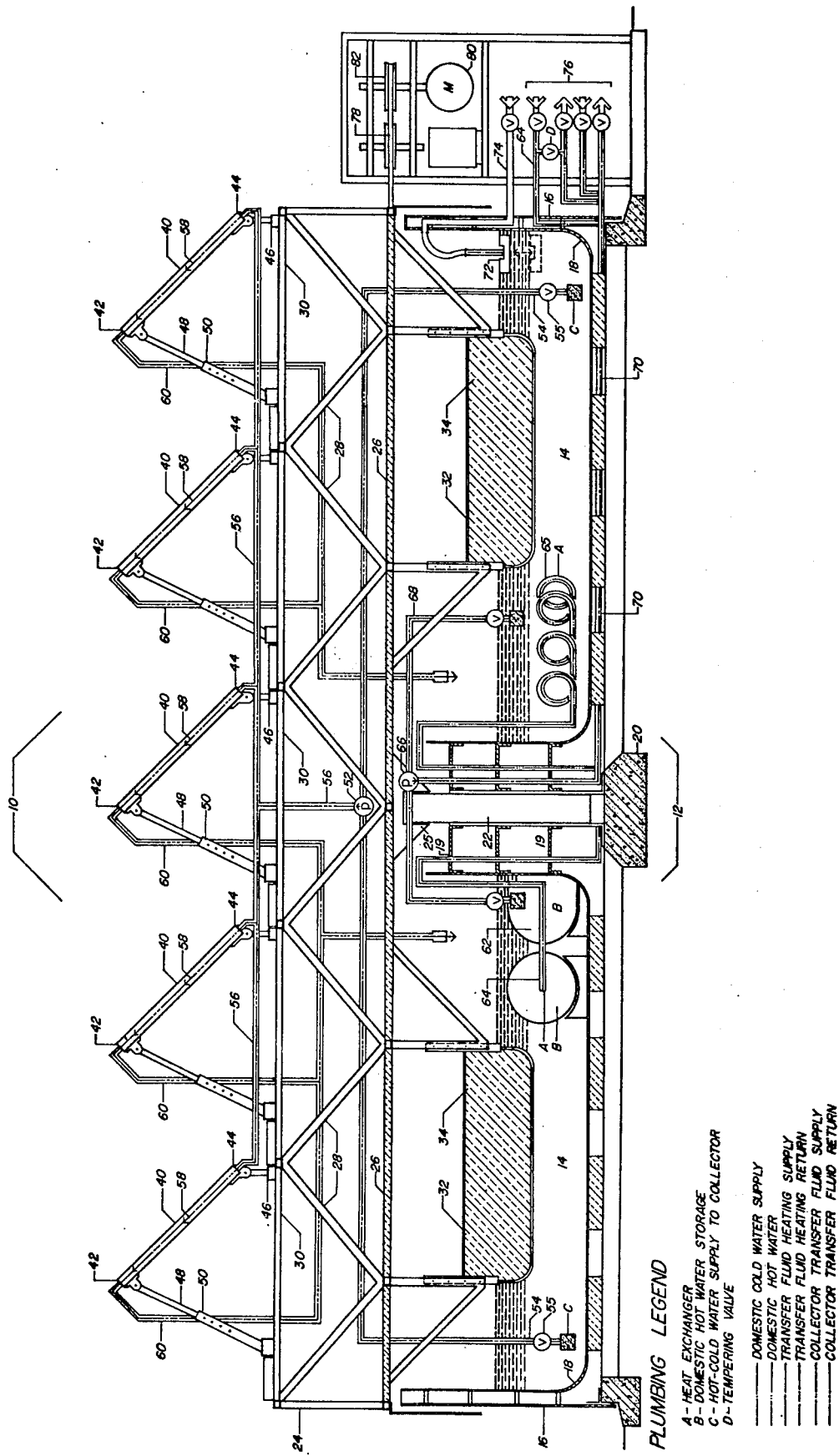
FIG. 2 is a side elevation, in cross-section, of a preferred embodiment of a solar collection and storage facility in accordance with the present invention.
Figure 3:
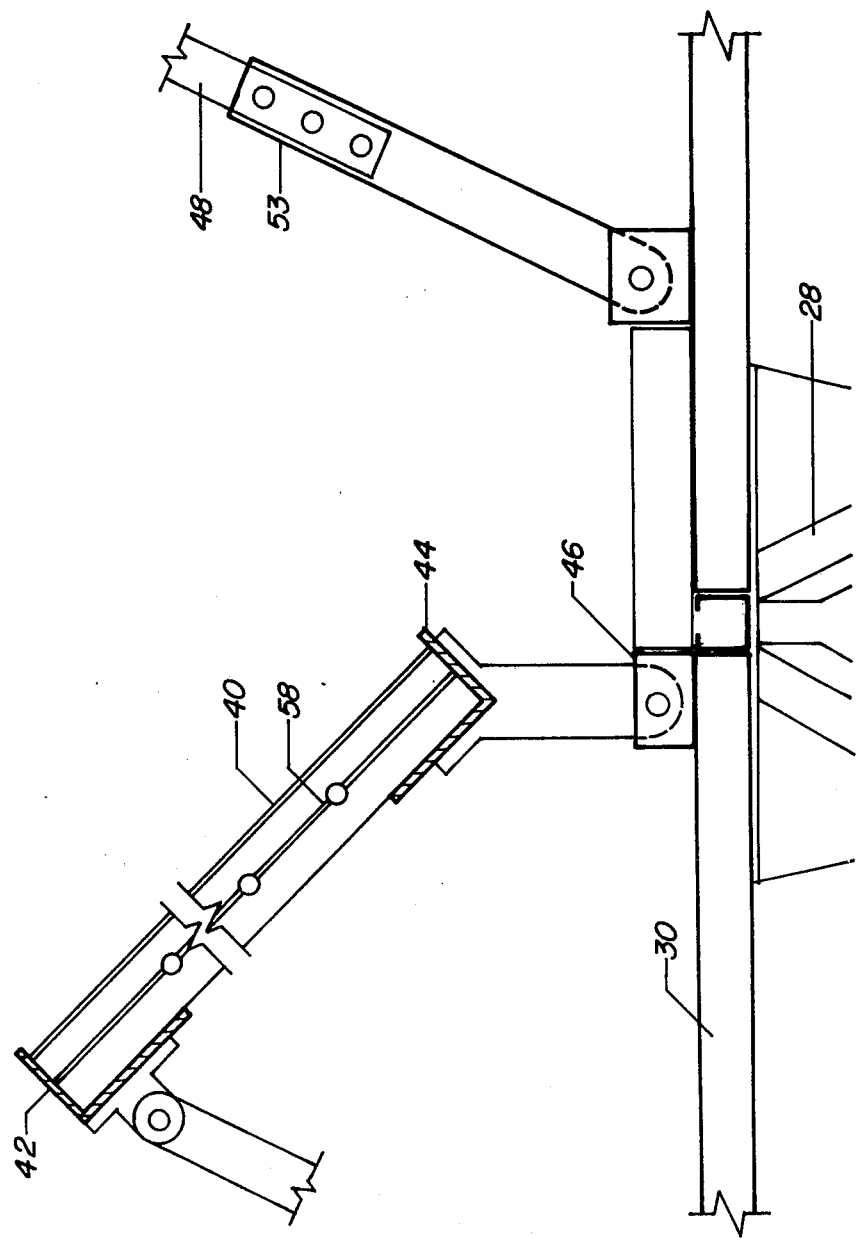

FIGS. 3(a) and 3(b) are side views of two embodiments a portion of the apparatus of FIG. 2.

Figure 4:
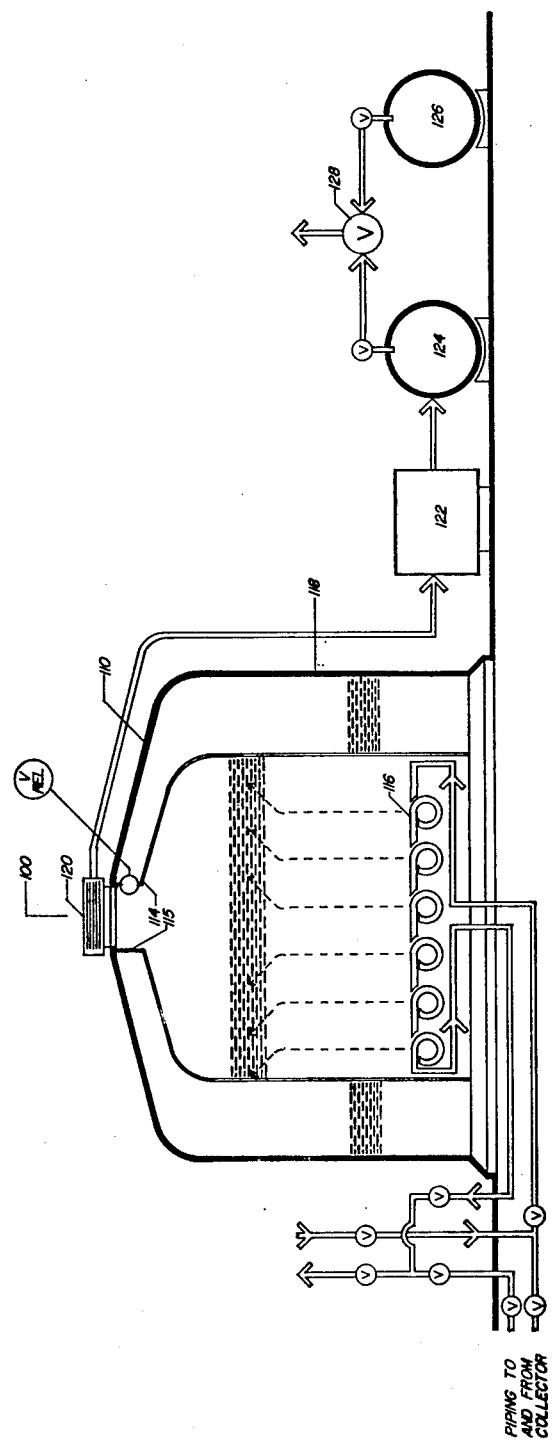

FIG. 4 is a side elevation, in cross-section, of a preferred embodiment of a methane gas generation facility in accordance with the present invention.

Figure 5:
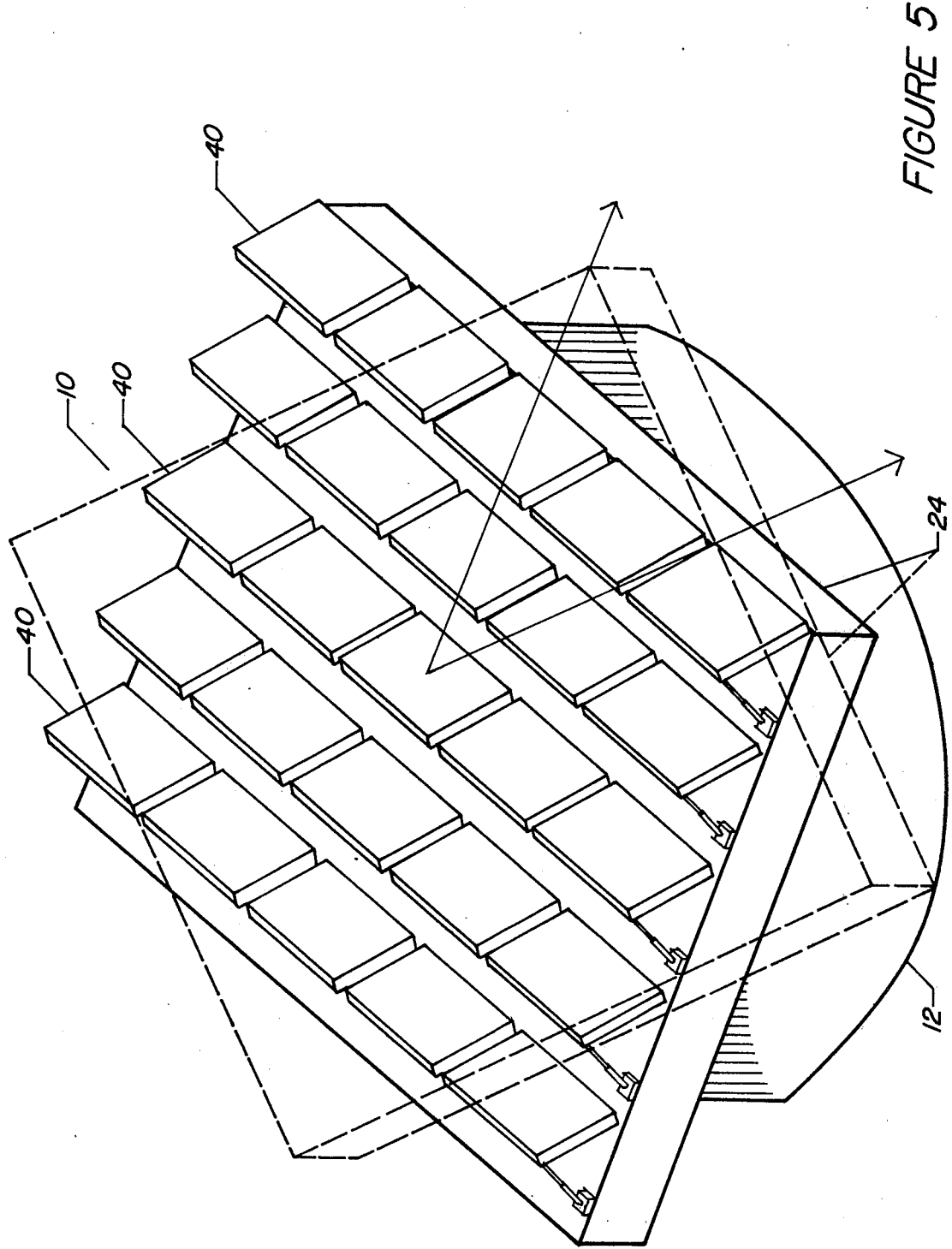

FIG. 5 is a perspective view illustrating the use of the solar collection facility illustrated in FIG. 2.

FIG. 6 is a flow chart illustrating a typical application of the system in accordance with the present invention.

DESCRIPTION OF THE PREFERRED EMBODIMENT

A preferred embodiment of the solar collection and storage facility in accordance with the present invention will be described with reference to FIGS. 1 and 2.

Figure 1:
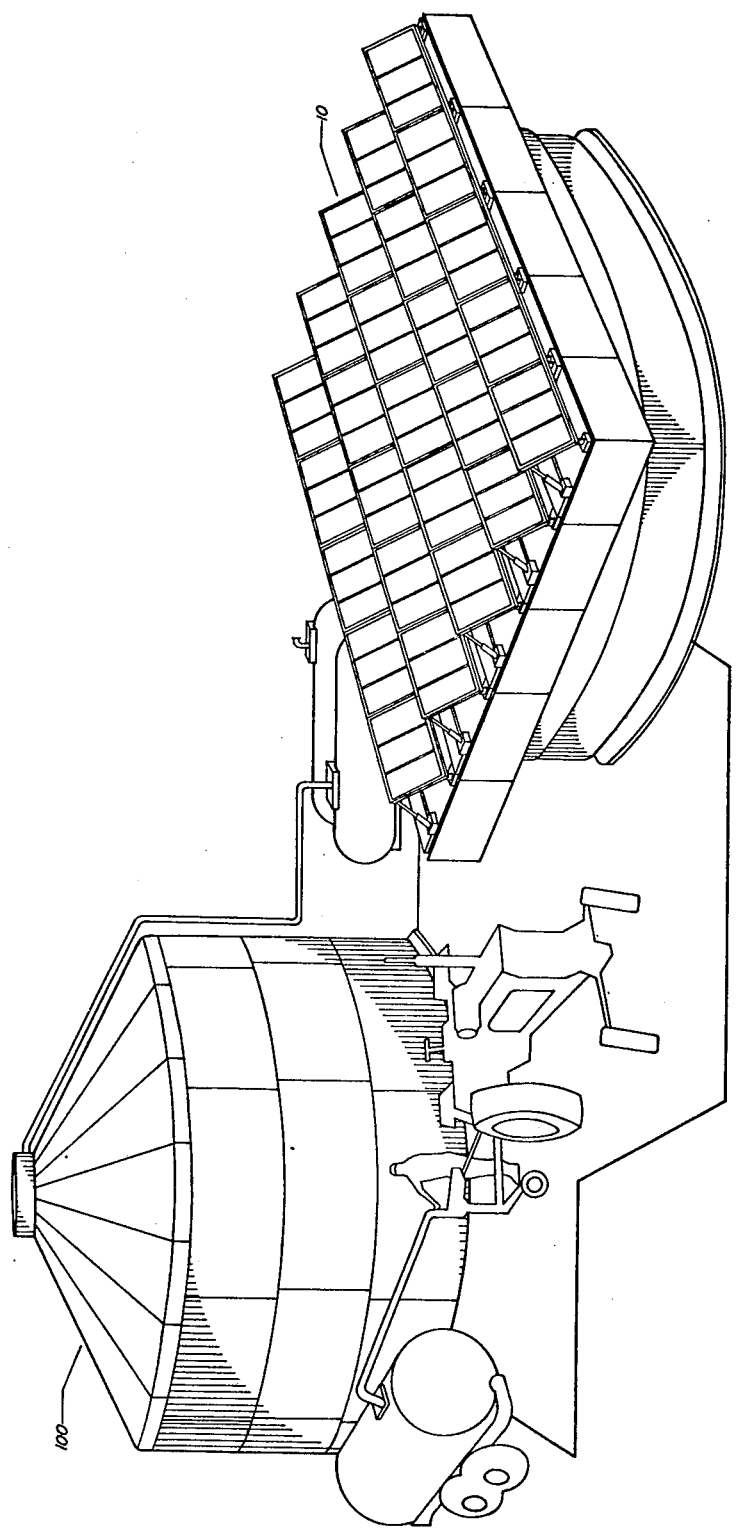
FIG. 1 is an overall perspective view illustrating the system of the present invention.

First noting FIG. 1, the system in accordance with the present invention includes a solar collection and storage facility, referred to generally as 10, which collects radiant energy from sunlight and converts this energy into heat. Thereafter, the heat energy is stored within the collector facility 10 and is thereafter transmitted to a methane gas generating facility 100, where the heat of radiation is used to accelerate the digestion of an organic waste slurry to effect methane gas generation by holding the temperature of the slurry at an optimal temperature.

With particular reference to FIG. 2, the solar collection and storage facility 10 includes a reservoir 14 for storing a good heat transfer fluid, such as water. The reservoir is formed of an outer tank 16 and an inner, non-corrosive tank 18 having a central collar 19. The facility 10 further includes a central footing 20 which supports a pivot shaft 22 extending through the collar 19 and slightly above the level of the inner and outer tanks, 16 and 18.

The facility 10 is further provided with a solar energy collector support, referred to generally as 24. The collector support 24 includes an insulating platform 26 which preferably comprises a lightweight, high heat insulation material such as a urethane-filled honeycombed insulation. The collector support 24 is supported on the pivot shaft 22 by a pivot sleeve 25. The collector support 24 is further provided with a supporting platform grid 30 formed of a plurality of structural elements 28, all integrally tied to the pivot sleeve 25. As is evident from FIG. 2, the entire support 24 and the solar collector assembly 40, referred to in greater detail below, is carried by the fluid 14 and is buoyed by floats 32 fixed underneath the platform 26. Each float 32 consists of an outer, non-corrosive shell and an inner, lightweight insulating material 34, such as spun glass.

In accordance with the present invention, the collector facility is provided with a plurality of flat solar collectors 40, each defined by opposing edge surfaces 42 and 44. The lower edge surface 44 of each flat plate collector 40 is supported by a pivot 46, such as a conventional ball joint, for example. The opposing edge 42 of each flat plate collector 40 is supported by an adjustable arm 48, the dimension of which may be changed by movement through a cylinder 50 associated with each adjustable arm. With specific reference to FIG. 3(a), the cylinder may comprise a hydraulic actuator 51 which is automatically operated responsive to an external pressure to move the adjustable arm 48 in the desired manner. Alternatively, as shown in FIG. 3(b), the cylinder may comprise a simple, manually operated cylinder 53 in which the adjustable arm 48 may be moved to one of several positions in order to elevate the opposing edge 42 of the flat plate collector 40 with respect to the plane of the platform 30.

Referring again to FIG. 2, the solar collection and storage facility 10 further includes means for pumping the heat transfer fluid 14 out of the reservoir 12 and through each flat plate collector 40. In the preferred embodiment, this means includes an intake pump 52 which is carried by the collector support 24. The facility 10 is further provided with intake pipes 54 extending into the transfer fluid reservoir 12 and communicating through the intake pump 52 to an input pipe 56 connected to each solar collector 40. Each solar collector 40 is provided with conventional plumbing within the collector (indicated by arrows 58 in FIG. 2), to transmit the heat transfer fluid through the collector and be heated in a well-known manner. The water exiting each flat plate collector 40 then passes into a return pipe 60 which returns the heated transfer fluid to storage in the reservoir 12.

A portable (domestic) water tank 62 is supported within the reservoir 12, and is provided with appropriate piping 64 to carry well water stored within the tank to locations remote from the collector 10. A heat exchanger 65 is coupled to the domestic hot water tank 62, in order to boost the heated stored water therein before it exits the collector facility 10 to be used externally for conventional home uses.

In order to use the heated transfer fluid 14 stored within the reservoir 12, a second pump 66 is provided to draw the heated transfer fluid 14 out of the reservoir 12 via a pipe 68 and through an output pipe 70 to points remote from the collector facility 10. The use of the water passing out of the output pipe 70 will be described in greater detail below with reference to FIGS. 3 and 5.

With continued reference to FIG. 2, the collector facility 10 is provided with a float valve 72 to detect the level of the supporting heat transfer fluid 14 within the reservoir 12. A filler pipe 74 is provided, and is connected to an external fill source. Conventional valving 76 are provided in the various lines connecting the reservoir 12 to control the flow of fluids in an appropriate manner.

Noting the extreme right hand portion of FIG. 2, the collector facility is provided with means for rotating the collector support 24 and thus the flat plate collector 40 so as to track the sun's movement in relation to the horizontal ground plane. In a preferred embodiment, this rotating means includes an endless band 78 which is wrapped about the circumference of the collector support 24, preferably in the plane of the lower platform 26. A time actuated drive motor 80 is provided, and engages the band 78 so as to rotate the platform support 24 and the associated flat plate collectors 40 so as to track the sun's horizontal plane movement. Movable pulley, including pulley 82, are provided to control the tension of the band 78 about the periphery of the collector support 24.

Reference is now made to FIG. 4. A methane gas generating facility in accordance with the present invention is referred to generally as 100 in FIGS. 1 and 4. This facility includes a double walled container 110 having an inner slurry tank 112 and an outer shell defining a void with respect to the inner tank. The inner tank 112 includes a tapered top 114, and an opening 115 at the upper extremity thereof. A heat exchanger 116 is positioned at the bottom of the inner slurry tank 112 and is coupled to the heat transfer fluid output line 70 from the collection facility 10 (FIG. 2).

The methane gas generating facility 100 further includes a vacuum pump 120 positioned in the opening 115 of the inner slurry tank 112, and a conventional gas scrubber 122 coupled to the output of the vacuum pump 120. A storage facility 124 receives the output of the methane gas scrubber 122, and is coupled with a propane storage facility 126 to a mixing valve 128.

Operation of the solar energy collection and storage facility 10 will now be described with reference to FIGS. 1, 2 and 5.

Initially, the reservoir 12 is filled with the heat transfer fluid 14, which serves as a low-friction bearing for the platform 26 and support 24. The drive motor 80 is then energized to rotate the collector support 24 to the desired pointing angle, for example, toward the east shortly after sunrise. The position of each flat plate collector 40 may then be adjusted by operation of the adjusting arm 48 and each associated cylinder 50. The pump 52 is then energized, causing the heat transfer fluid 14 to be drawn out of the reservoir 12 and through the flat plate collectors 40 via the above described plumbing. The heated transfer fluid is then returned to the reservoir 12, and at such time as the total amount of fluid in the reservoir has reached a desired temperature level, the second pump 66 may be energized to cause the water to be pumped out of the reservoir 12 and through the output pipe 70. It will, of course, be understood that the predetermined temperature will depend on the specific end use of the heated transfer fluid, and will vary between applications. This function of the system may be controlled automatically, through appropriate temperature sensors located within the reservoir 12, which electrically control the operation of the pumps 52 and 66. It will further be understood that should an upper limit on the temperature of the heat transfer fluid 14 and the reservoir 12 be desired, operation of the pump 52 may also be controlled so as to maintain the temperature of the transfer fluid 14 within an acceptable range.

After the sun has moved to a substantially different position in the solar day, it is then feasible to rotate to entire collector assembly to point all of the flat plate collectors 40 in a different direction, as is shown in FIG. 5. Operation of the adjustable arm 48 may also be desired at this time, although such may not be essential for every horizontal plane pointing change. It will be understood by those skilled in the art that the pointing angle of the flat plate collector may be automatically controlled by appropriate programming and operation of the drive motor 80 during the solar day, and corresponding control over operation of the adjusting arm 48 in an appropriate manner. In this way, the efficiency of all of the flat plate collectors 40 may be greatly increased over a fixed configuration.

Operation of the methane gas generating facility 100 will now be described with reference to FIG. 4. As referred to earlier, the hot transfer fluid 14 through the output 70 from the solar collector facility 10 is passed into the heat exchanger 116 associated with the methane generation facility 100. Preferably, the heat exchanger is controlled so as to provide a temperature of about 92 degrees centigrade at all times, in order to facilitate the digestion of the organic waste slurry contained within the slurry tank 112. As a result of this digesting process, methane gas is generated and is collected in the opening 115 by the vacuum pump 120, and is thereafter transmitted to the scrubber system 122. After scrubbing, the methane gas is then passed into the storage tank 124. Although not essential, the collected methane gas may then be mixed in appropriate amounts with propane gas from the propane storage facility 126 in the mixing valve 128 for subsequent appropriate end uses.

Reference is now made to FIG. 6, which illustrates a typical application of the system in accordance with the present invention. In the application shown in FIG. 6, the system of the present invention is utilized in a farm environment, having a dairy, a farm house and a barn; and further is used to operate a tractor capable of receiving a methane-propane mixture for use in an internal combustion engine. The hot water from the collector facility is used to facilitate the generation of methane gas, as is described above, and is also used to operate a hot water fired chilling system to cool certain facilities, such as the dairy and farm house. The hot water is also used for appropriate needs in these buildings. It will be understood that the organic waste from a feed lot, the dairy or similar associated uses is stored in the outer shell of the double walled tank 110, and is then pumped into the slurry tank 112 for subsequent digestion and methane gas generation.

We claim:
1. In combination:
   a reservoir;
   a fluid stored in said reservoir;
   a platform carried by said fluid;
   a solar energy collector comprising at least one flat plate collector carried by said platform;
   fluid conducting means in said solar collector for receiving energy collected from solar radiation and heating a fluid passing therethrough;
   means communicating between said reservoir and said fluid conducting means whereby said fluid is heated by said collector and stored in said reservoir;
   means for rotating said platform; and
   means for elevating one edge of said flat plate collector.

2. The combination recited in claim 1 wherein said rotating means comprises:
   a fixed shaft extending through said reservoir;
   means coupling said platform to said shaft; and
   means engaging the periphery of said platform for rotation thereof about said shaft.

3. The combination recited in claim 2 wherein said periphery engaging means comprises:
   an endless band about the circumference of said platform;
   a drive motor engaging said endless band for rotating said platform; and
   an adjustable pully engaging said endless band for changing the tension of said band against the periphery of said platform.

4. The combination recited in claim 2 wherein said elevating means comprises:
   an adjustable arm engaging said one edge of said flat plate collector; and
   means for changing the length of said adjustable arm to thereby elevate said one edge with respect to the plane of said platform.

5. The combination recited in claim 4 further comprising buoyant means supported on the underside of said platform and carried by said fluid.

6. The combination recited in claim 5 wherein said collector comprises an array of said flat plate collectors.

7. The combination recited in claim 1 further comprising a buoyant material joined to said platform and floating in said reservoir.

8. The combination recited in claim 1 further comprising:
   a slurry tank;
   a heat exchange coil in said tank; and
   means coupling said reservoir with said coil whereby heated fluid is moved from said reservoir through said coil to effect heating of a slurry in said tank.

9. The combination recited in claim 8 further comprising means coupled with said tank for collecting methane gas generated by heating and digesting of said slurry in said tank.

10. The combination recited in claim 9 wherein said collecting means comprises:
    said tank having an upward taper and an opening at the top thereof; and
    a vacuum pump or other suitable device in said opening for collecting methane gas passing into said opening.

11. The combination recited in claim 10 further comprising an outer shell surrounding said tank for storing undigested slurry prior to pumping into said tank.

12. The combination recited in claim 11 further comprising:
    means for storing said methane gas;
    a container for a supply of propane gas; and
    means for mixing said methane and propane gases as a fuel.

13. The combination recited in claim 1 further comprising:
    a float valve in said reservoir for detecting the level of fluid therein; and
    means operable responsive to said float valve for adding fluid to said reservoir.

14. The combination recited in claim 1 further comprising
    a potable water storage container in said reservoir;
    heat exchange means in said reservoir and coupled to said storage container, whereby water in said container may be heated by said fluid.

15. The combination recited in claim 1 wherein said platform comprises a heat insulative material.

16. Solar energy collection apparatus comprising:
    a platform;
    a plurality of flat plate collectors supported by said platform, each collector having a fluid conductor therein for transfering heat of radiation to a fluid passing therethrough;

means for changing the angle of all of said flat plate collectors with respect to the horizontal plane;

means for rotating said platform including low-friction bearing means for supporting said platform, and means engaging the periphery of said platform for rotation about the center thereof; whereby the efficiency of said collectors may be optimized by utilization of said angle changing and rotation means to position said flat plate collectors with respect to incident solar radiation.

17. The apparatus recited in claim 16 wherein said low friction bearing means comprises:

a reservoir;

a fluid within said reservoir; and wherein said platform is carried by said fluid.

18. The combination recited in claim 17 further comprising means communicating between said reservoir and said fluid conductor whereby said heated fluid is stored in said reservoir.

19. The apparatus recited in claim 16 wherein said angle changing means comprises a plurality of adjustable arms, each coupled to an edge of a corresponding one of said flat plate collectors to effect rotation of said flat plate collector with respect to a plane generally parallel to the horizontal plane.

20. The apparatus recited in claim 16 further comprising:

a slurry tank;

a heat exchange coil in said tank; and means coupled with said fluid conductor to move heated fluid from said collector through said heat exchange coil to effect heating of a slurry in said tank.

21. In combination:

a slurry tank;

heat exchange means in said tank;

a platform;

a solar energy collector comprising a parallel array of flat plate collectors carried by said platform;

means engaging the periphery of said platform for rotation about the center thereof means for elevating one edge of each of said flat plate collectors;

a fluid conductor within each said flat plate collector for transfering heat of radiation to a fluid passing therethrough;

means coupling said fluid conductor with said heat exchange means; whereby said heated fluid is moved from said fluid conductor through said heat exchange means to effect heating of a slurry of organic materials therein, causing generation of methane gas within said tank.

22. The combination recited in claim 21 further comprising:

a reservoir;

an amount of said fluid stored in said reservoir; and means coupled between said reservoir and said fluid conductor whereby said heated fluid may be stored in said reservoir.

23. The combination recited in claim 22 wherein said platform is carried by said fluid in said reservoir.

24. Apparatus for collecting solar energy comprising:

a reservoir;

a fluid stored in said reservoir;

a platform carried by said fluid in low-friction relationship therewith;

a plurality of flat plate collectors supported by said platform;

fluid conducting means within each said collectors for transferring heat of radiation to a fluid passing therethrough;

means for pumping said fluid from said reservoir through said fluid conducting means;

means for returning the fluid from said collectors to said reservoir;

means for rotating said platform about a central axis associated therewith.

* * * * *